(12) United States Patent
Porat

(10) Patent No.: US 7,718,642 B2
(45) Date of Patent: *May 18, 2010

(54) AIDS PROPHYLACTIC LUBRICATING COMPOSITION

(76) Inventor: Michael Porat, 52 Hamitnadey Street, Afeka, Tel Aviv 69690 (IL)

( * ) Notice: Subject to any disclaimer, the term of this patent is extended or adjusted under 35 U.S.C. 154(b) by 1283 days.

This patent is subject to a terminal disclaimer.

(21) Appl. No.: 10/627,968

(22) Filed: Jul. 28, 2003

(65) Prior Publication Data

US 2004/0072910 A1    Apr. 15, 2004

Related U.S. Application Data

(63) Continuation-in-part of application No. 07/978,671, filed as application No. PCT/US93/00826 on Feb. 5, 1993, now Pat. No. 6,624,198.

(51) Int. Cl.
*A01N 43/00* (2006.01)
*A01N 37/52* (2006.01)
*A01N 43/36* (2006.01)

(52) U.S. Cl. .................. 514/210.01; 514/635; 424/325

(58) Field of Classification Search .................. 514/554
See application file for complete search history.

(56) References Cited

U.S. PATENT DOCUMENTS

| 4,242,359 | A | * | 12/1980 | Cooper et al. | ................ 514/659 |
| 4,602,042 | A | * | 7/1986 | Chantler et al. | ............. 514/635 |
| 5,342,617 | A | | 8/1994 | Gold | |
| 6,624,198 | B1 | * | 9/2003 | Porat | ........................... 514/635 |

FOREIGN PATENT DOCUMENTS

WO     93/15728     8/1993

OTHER PUBLICATIONS

Harbison et al, J. Acquired Immune Deficiency Syndrome, 2:16-20 (1989).
Matindale: The Extra Pharmacopoeia, 29th Ed. (1989), pp. 416, 1356-1357.
Matindale: The Extra Pharmacopoeia, 26th Ed. (1972), pp. 1521-1523, 1526, 1530.
CA 115:238679h, Abstract of Suzuki et al, Bull Yamaguchi Med. Sch. (1990), 37(3-4), 95-100.
CA 82:52123e, Abstract of Shenkai, Proc. Soc. Exp. Biol. Med. (1974), 147(1), 201-4.
Shubair et al, Gynecol. Obstet. Invest. (1992) 34:229-233.
Abstract of Kreiss et al, Int. Conf. AIDS (Canada), Jun. 4-9, 1989, 5:51.
Abstract of Kreiss et al, JAMA, Jul. 22-29, 1992, 268(4), 477-482.

* cited by examiner

*Primary Examiner*—Sreeni Padmanabhan
*Assistant Examiner*—Timothy E Betton
(74) *Attorney, Agent, or Firm*—Dennison, Schultz & MacDonald

(57) ABSTRACT

A prophylactic lubricant composition for use during sexual relations, includes:
 a) lubricant effective to reduce friction, thereby reducing the rupture of blood vessels during sexual relations,
 b) an effective amount of spermicidal antiseptic active against HIV and other viruses, said antiseptic destroying the human immunodeficiency virus and other viruses, said antiseptic immobilizing the sperm and reacting with vaginal mucosa to form a barrier to the penetration of sperm cells into the uterus; and
 c) an effective amount of a fungicide to prevent the growth of fungi in the vagina which grow in the absence of natural bacterial flora destroyed by the antiseptic;
said composition having no substantial detrimental effect.

15 Claims, No Drawings

AIDS PROPHYLACTIC LUBRICATING COMPOSITION

This application is a continuation-in-part of U.S. application Ser. No. 07/978,671, filed Nov. 7, 1994 now U.S. Pat. No. 6,624,198 and incorporated herein by reference, which is a filing under 35 USC 371 of PCT/US93/00826, filed Feb. 5, 1993.

BACKGROUND OF THE INVENTION

The present invention relates to an antiseptic lubricant composition for use in sexual relations. The lubricant composition of this invention reduces the risk of infection by viruses such as herpes simplex (HSC), cytomegalovirus (CMB), influenza A, parainfluenza, hepatitis B (HBV) and particularly human immunodeficiency virus (HIV). The lubricant composition of this invention, in addition to destroying bacteria and viruses, prevents pregnancy by destroying sperm cells and furthermore prevents any surviving sperm cells from entering the uterus. The present invention also relates to a method for reducing the risk of infection by lethal viruses during sexual relations and reducing the risk of pregnancy, and to devices containing antiseptic lubricant.

In the last decade, the rapid spread of the HIV and the accompanying concern of its terrifying consequences for mankind, have created a sense of urgency to find both short and long term solutions for this modern plague. There are many ways in which the HIV and some other viruses are transmitted by people. One of the most common forms of transmission is by sexual contact. During intercourse, there are basically three ways in which the HIV can be transmitted from one person to another. One way is by the friction caused by a penis penetrating into the vagina, which is capable of tearing small and sometimes invisible blood vessels (capillary vessels) of both sexual partners. The blood from these vessels is consequently commingled and the HIV present in one partner is transferred via the blood to the other partner. As far as is known, the HIV develops mainly in the blood cells, although it is transferred and transmitted by body fluids. A second way for transmitting the HIV is through the body fluids which the body secretes during sexual relations. A third way is via the semen. It has been found that the HIV can reside in the spermatophore (sperm-liquid) or even on or in the spermatocide (sperm cell). Thus, the HIV which resides in the sperm may infect the other sexual partner.

HIV, herpes and similar viruses are surrounded by three envelopes. These envelopes are composed of the same material as that of the human cell walls. When the outside envelope of the virus comes into contact with the outer cell wall of humans, the human cell recognizes the virus as part of itself and absorbs it, and proceeds to produce more viruses until they overflow. The excess viruses are then expelled from the human cell and search for other host cells which will continue to produce more viruses.

The most common and so far most effective way of avoiding infection by HIV and other related viruses during sexual relations is by the use of a condom put on prior to copulation. The condom prevents direct contact between sexual organs and body fluids of the partners and also retains the sperm and prevents it from entering the vagina and eventually the uterus. As far as is known, the HIV cannot penetrate the rubber material from which condoms are made. Only if the condom is defective, for example perforated or otherwise damaged, can transmission of the virus occur. Many people, however, do not like using a condom, mainly because of the odd sensation of indirect contact with the sex partner, which in many cases interferes with and/or diminishes sexual satisfaction. It is also known that to reduce friction and increase sexual satisfaction during intercourse, people avail themselves of lubricants which may be soluble, like K-Y (a Trademark product Johnson & Johnson) or a non-soluble fatty lubricant, like soft paraffin. This is particularly the case with atrophy and in elderly people, who use lubricants to complement the diminished quantities of natural lubricants produced as compared with the situation in younger people.

Gels and foams for application before or during sexual intercourse are known, some of which contain spermicides, such as Nonoxynol-9. Many disinfectants are also known to be effective against viruses and are used as antiseptics in topical applications in concentrations that are not harmful to body tissues. Among the known disinfectants are the previously mentioned Nonoxynol-9, as well as Benzalkonium Chloride, Povidone Iodine, Nitrofurazone and chlorhexidine salt. These disinfectants, and others not mentioned but found in medical pharmacopoeias, have similar disinfecting characteristics, although they differ chemically and react differently to body tissues. The disinfectant compositions are generally used as antiseptics and applied topically for destroying bacteria and/or viruses that already exist in the area to which they are applied and to maintain these areas free of such organisms, to prevent possible future infections such as in the treatment of wounds and burns. Some compositions containing disinfectants are also known for use in disinfecting the sexual organs. These disinfectants, however, have not been successful in preventing HIV infections resulting from sexual relations. It was known to those in the field, that merely applying an antiseptic, that is effective against HIV in topical applications, to the sexual organs during sexual relations does not prevent HIV infection. In a study by J. Kreiss et. al, JAMA 268: 4, 477-82, Jul. 22-29, 1992, nonoxynol-9, a well known antiseptic spermicide, was tested in Nairobi prostitutes for use in preventing heterosexual transmission of HIV. Although nonoxynol-9 is known to be quite effective in killing HIV topically, it did not prevent HIV transmission when used as contraceptive, i.e. during sexual relations. Thus there appears to be a clear difference between topical activity against HIV and actual prevention of transmission of HIV during sexual relations.

U.S. Pat. No. 4,602,042 to Chantler, et al. claims a contraceptive method comprising applying to the mucus in the vagina a spermicidal compound such as chlorhexidine.

M. A. Harbison, et al. in J. ACQUIR. IMMUN. DEFIC. SYNDR. Vol 2, no. 1, 1989, pages 16-20, demonstrated topical decontamination and deactivation of HIV in cell culture systems with antiseptic compounds such as Betadine and chlorhexidine glucagon in dilute solutions. Among the many compositions tested topically against HIV there was a single gel composition containing Betadine antiseptic which was effective only at a much higher concentration of Betadine than ordinary solutions containing this antiseptic. Harbison, et al., although showing that these antiseptic materials are effective against HIV when applied topically, does not suggest a prophylactic spermicidal lubricating composition for use during sexual relations. U.S. Pat. No. 5,342,617 to Gold discloses a water based lubricant composition for application, inter alia, in the vagina. The composition is bases on high molecular weight polyethylene oxides in combination with polyhydroxy humectants. This lubricating base composition is the essence of Gold's disclosure. In order to prevent bacterial, mold or fungal growth in the humectant, stabilizers or sterilizing inhibitors are added, i.e. to protect the composition from deteriorating and prolong its shelf life. Parabens were particularly preferred for this purpose. The patent also mentions, by the way, that spermicides may be added to the composition to inhibit pregnancy. However, no spermicides were listed, exemplified or claimed, nor were any effective concentration of these suggested.

SUMMARY OF THE INVENTION

One problem of using a disinfecting agent in the area of the female genitals is that the tissues in the vagina of fertile women are normally regenerated frequently and antiseptic agents in general inhibit the vaginal tissues from regenerating.

Another problem may arise when using disinfectants in the area of the female genitals is that they destroy the natural flora of bacteria present in the area, which flora prevent the growth of fungi. With the destruction of the bacteria, there is a tendency for the fungi to proliferate.

Vaginal infections are a common gynecological complaint. Infectious vaginitis may result in increased vaginal discharge, vulvar irritation and pruritus, external dysuria, and unpleasant odors. A common cause for this is a substantial increase of fungi in the vagina, including *Candida, Gardnerella vaginalis*, and *anaerobes*. Indeed *Candida albicans* causes more than 90% of vaginal yeast infections, and, other, non-*Candida* species may also cause infection.

The present invention is premised on the discovery that when selected antiseptically active materials together with suitable fungicides are incorporated in lubricants for use in sexual relations, a number of advantages are obtained which make the sexual relations safe and worry-free, both from the risk of contracting a serious viral disease such as the HIV, and from the risk of becoming pregnant. The antiseptic material for use in this invention should be effective in concentrations that are safe and acceptable for use in contact with sexual organs. It must have the ability to kill bacteria and viruses at such concentration levels. It must have spermacidal properties and furthermore must have the additional feature of reaction with vaginal mucosa to seal the cervical passage against penetration of any residual or surviving sperm cells. The fungicide prevents growth of fungi which can cause ulceration of the vagina.

Medical and pharmaceutical studies have shown that the HIV develops mainly in the blood cells and is carried by various body fluids to other cells. When the antiseptic lubricant of this invention is applied to the sex organs, a number of advantages are obtained. The lubricant reduces the friction between the penis and the vaginal wall, thus reducing the rupture of blood cells which might otherwise occur and therefore reducing the amount of blood that is commingled. Any blood that does appear is immediately disinfected by the active antiseptic ingredient. Furthermore, the antiseptic compound also kills any bacteria and viruses in the body fluids which are present or are generated during intercourse. The selected antiseptic compound, being a spermicide as well, destroys the sperm and any virus it may carry inside the vagina, and last but not least, the antiseptic compound reacts with the mucosa to create a barrier in the cervix, preventing any surviving sperm from entering the uterus. The vagina is converted into a "sealed bag" by creating a barrier which prevents sperm from passing through the cervix and any viruses present in the sealed vagina will subsequently be destroyed.

The genital lubricant composition of this invention effectively prevents transmission of HIV and other viral and bacterial infections during intercourse, without risking fungal infections such as the vaginal yeast infections due to *Candida albicans*, for example. It provides significant protection against sexually transmitted diseases and pregnancy where a condom is not worn, and an additional layer of protection when used with conventional prophylactics.

It is the object of the present invention to provide a prophylactic lubricating composition for use in sexual relations.

Another object of the invention to provide a lubricating composition that enhances sexual satisfaction during intercourse.

A further object is to provide a lubricating composition that prevents infection, and avoids pregnancy.

By using a single prophylactic lubricating composition, as defined hereinafter, one accomplishes the following:

1. Provides proper lubrication.
2. Destroys bacteria and viruses.
3. Prevents the mobility of sperm cells.
4. Prevents the penetration of sperm cells into the uterus.
5. Prevents fungi from developing in the vagina.
6. Safe use without harmful side effects.

Typically, the genital lubricant composition contains a lubricant, a spermicide, an antibiotic agent and a fungicide. The lubricant may comprise any genital lubricant base as known in the art, such as an aqueous base, a petroleum base or a silicone base.

The preferred antibiotic is a chlorhexidine salt, having antiviral properties. Unlike lubricants and other compositions of chlorhexidine salts known, the present invention includes a fungicide at a suitable concentration to prevent the yeast and other fungal infections that commonly result from use of antibiotic agents such as chlorhexidine salt, which, when used alone, kill lactobacilli and allow fungi to proliferate.

DETAILED DESCRIPTION OF THE INVENTION

In accordance with the present invention, there is provided a prophylactic lubricant composition for use during sexual relations, comprising:

a) a lubricant effective to reduce friction, thereby reducing the rupture of blood vessels during sexual relations, b) an effective amount of spermicidal antiseptic active against HIV and other viruses, said antiseptic destroying the human immunodeficiency virus and other viruses, said antiseptic immobilizing the sperm and reacting with vaginal mucosa to form a barrier to the penetration of sperm cells into the uterus;

c) an effective amount of a fungicide to prevent the growth of fungi in the vagina which grow in the absence of natural bacterial flora destroyed by the antiseptic; said composition having no substantial detrimental effect.

The tissues in the vagina of fertile women are normally regenerated frequently and antiseptic agents are known to often inhibit the vaginal tissues from regenerating. Therefore lubricating compositions for use in the area of the vagina should have the same pH as the vagina itself, in order to eliminate this problem. The antiseptic lubricant composition of this invention should also preferably contain an alcohol or mixtures of alcohols, to enhance the activity of the disinfectant. Preferably water soluble lubricants are used, since any stains that they may form on clothing or sheets are readily washed out with water and their use is particularly recommended when rubber or latex prophylactics are used, such as condoms or diaphragms. The preferred lubricant is propylene glycol, but other water soluble lubricating materials, as known in the art, such as glycerine, may also be used, alone or in combination. Although water soluble lubricants are preferred, fatty lubricants like soft paraffin may also be used if desired. In fact, any effective lubricant or combination of lubricants acceptable for cosmetic applications may be used.

The spermicidal antiseptic compounds in accordance with this invention are preferably chlorhexidine and its salts, particularly the gluconate or digluconate salts. Chlorhexidine and its salts are well described in the medical literature as being effective against a wide range of viruses and bacteria and have been used in the form of antiseptic solutions, creams and gels for topically disinfecting wounds, skin, mouth, urethra and other parts of the body. Chlorhexidine is known not to accumulate in the blood and does not enter mammalian cells. When applied to the human genitals in concentrations even up to 4%, it does not produce any undesirable side effects.

During ovulation, the female body produces a mucous in the cervix which selectively allows sperm cells to penetrate to the uterus. At all other times, the cervix does not allow penetration of sperm cells or semen into the uterus. Chlorhexidine, on the other hand, diffuses into the cervical mucous, creating a suspension. This suspension restricts the penetration of sperm cells during ovulation and causes them to rapidly lose their mobility. This effect occurs at concentrations of chlorhexidine in excess of 0.1%. Thus, by using chlorhexidine as the active antiseptic compound in accordance with the present invention, the chlorhexidine diffuses into the cervical mucous prior to the ejection of semen and in effect creates a "sealed bag" in the vagina, which retains all body secretions including semen. Any viruses present will be destroyed by the chlorhexidine. Chlorhexidine, in concentrations above 0.1%, effectively destroys the envelope of viruses and in so doing prevents the virus from penetrating the human cell.

The preferred fungicide is methyl paraben which does not harm human tissues and destroys fungi which develop in the absence of bacterial flora. However, other known and approved fungicides may also be used in appropriate doses. Examples of other fungicides which may be used instead of methylparaben, include isopropyl paraben, miconazole and miconazole-nitrate, for example.

A preferred antiseptic lubricant composition in accordance with this invention comprises a mixture of propylene glycol or glycerine, or both, with water, mixed with carbomethyl cellulose (CMC) or hydroxyethyl cellulose (HEC) or both. These are formulated with chlorhexidine gluconate or digluconate and methylparaben. Such a composition can have the following concentrations:

| | |
|---|---|
| Chlorhexidine salt | 0.1% to 5% |
| Methylparaben | 0.1% to 1.0% |
| Propylene glycol | 2.0% to 6% |
| Glycerine | 5.0% to 15% |
| CMC or HEC | 0.5% to 2.0% |
| Purified water | To complete to 100% |

Another preferred lubricant composition has the following concentration of ingredients:

| | |
|---|---|
| Chlorhexidine digluconate | 0.2% to 6% |
| Methylparaben | 0.15% |
| Propylene glycol | 4.0% |
| Glycerin | 11.0% |
| HEC | 1.25% |
| Purified water | To complete to 100% |

The lubricant composition should be easy to apply and should not disturb the sexual act, without diminishing the antiseptic potency. (Most disinfectants are sensitive to light and should be packaged in sealed containers protected from light and air). It is therefore suggested to package the lubricant in a single use disposable sterile sealed packet. Sterilization can take place by heating the sealed packet for ten hours at 70° C. to give a S.A.L. of $10^{-10}$.

A commercial lubricating gel composition in accordance with this invention, available under the name Gel-X™, has the following composition:

| | |
|---|---|
| Chlorhexidine Guconate | 0.50% |
| Methyl Paraben | 0.25% |
| Glycerine | 11.00% |
| Propylene Glycol | 4.00% |
| Natrosol HHRB | 1.25% |
| Deionized Water | 83.00% |

Tests were performed to compare the effects of the combination of antiseptic with fungicide against either component alone, on vaginal flora.

Because in vivo testing on humans is not permissible according to the Helsinki Accord without special approval, which would not be granted where ulceration is the expected result, in vitro tests were performed as follows.

The following nine compositions were prepared.

1. Chlorhexidine Gluconate (B.P. 20% I.C.I.), 0.5%; Methylparaben (B.P. N.F. Merck) 1%
2. Chlorhexidine Gluconate (B.P. 20% I.C.I.) 0.5%
3. Benzalkonium Chloride (U.S.P. XXIII 50% Caelo) 1%
4. Chlorhexidine Gluconate (B.P. 20% I.C.I.) 0.5%; Miconazole Nitrate (B.P. U.S.P. Abic) 1%
5. Nonoxynol-i (B.P. Teva) 12.5%
6. Benzalkonium Chloride (U.S.P. XXIII 50% Caelo) 1%; Methylparaben (B.P. N.F. Merek) 1%
7. Nonoxynol-9 (B.P. Teva) 12.5%; Propylparaben (Niposol (D M U.S.P. Nipa) 1%
8. Methylparaben (B.P. N.F. Merek) 1%
9. Miconazole Nitrate (B.P. U.S.P. Abic) 1%

In the above compositions, B.P. stands for British Pharmacopoeia, U.S.P. stands for United States Pharmacopoeia and N.F. stands for National Formulary (U.S.).

Compositions 1, 4, 6 and 7 contain active dosages of antibiotic agents and fungicides, and are suitable for use in genital lubricants in accordance with the claimed invention, whereas compositions 2, 3, 5, 8 and 9 contain either antibiotic agents or fungicides, but not both.

The above compositions were prepared as solutions made up in purified water, with the exception that the methylparaben and propylparaben were first diluted in 10% aqueous propylene glycol.

Cultures of microorganisms were prepared as follows:

1. *Staphylococcus Aureus* (oxid, culti loops, 022 396) on "DIFCO" Baird Parker agar base, incubated at 370° C. for one day.
2. *Candida Albicans* on "DIFCO" Agar Sabouraud incubated for three days at 30° C.
3. *Lactobacillus* on "DIFCO" APT Agar, incubated for three days at 35° C.

In each case the microorganisms were inoculated on the suitable medium in a quantity of 1 ml. containing approximately 100,000 microorganisms. Ten plates were used for each series, nine for the compositions to be tested and one for a control.

The cultures were climatized for one hour on a shelf of a chamber at 30° C. to 35° C.

A hollow depression of 8 mm diameter was formed at the center of each plate, and the depressions were respectively inoculated with 0.05 ml test compositions 1 through 9 and one plate was used as a control. The plates were then incubated with cultures 1, 2 and 3 at 35° C., 25° C. and 35° C. respectively, and measurements were taken from the lip of the hollow, up until the time of microbial growth was evident. The experiment conducted with seven such series.

After an incubation period of 24 hours, initial results were already apparent. After 48 hours, growth was evident on all cultures and the average results (of seven trials) are shown in the Table below:

TABLE

AVERAGE MEASUREMENTS OF EMPTY ZONES FOLLOWING MICROBIOLOGICAL GROWTH AFTER 48 HOURS:

| COMPOSITION | S. AUREAUS | CANDIDA | LACTOBACILLUS |
|---|---|---|---|
| CONTROL | 0 mm | 0 mm | |
| 1 | 17.0 mm | 14.0 mm | 14.4 mm |
| 2 | 9.9 mm | 3.1 mm | 14.3 mm |
| 3 | 6.1 mm | 2.1 mm | 17.3 mm |
| 4 | 7.3 mm | 15.6 mm | 14.4 mm |
| 5 | 4.9 mm | 0.6 mm | 10.7 mm |
| 6 | 8.0 mm | 16.4 mm | 17.1 mm |
| 7 | 2.1 mm | 12.7 mm | 10.1 mm |
| 8 | 1.1 mm | 18.6 mm | 2.1 mm |
| 9 | 0.3 mm | 16.4 mm | 2.3 mm |

The controls show that microorganism growth takes place over the entire plate without any inhibition, as is evidenced by the absence of empty zones.

Compositions 8 and 9 containing (different types of) fungicide, but no antibiotic agent were ineffective in controlling the growth of *S. Aureaus* and *Lactobacillus*, although very effective in inhibiting the growth of *Candida*. Compositions 2, 3 and 5 containing known spermicides, definitely inhibited the growth of Lactobacillus, somewhat suppressed the growth of *S. Aureaus*, and permitted significant growth of *Candida*.

Only compositions 1, 4, 6 and 7, were effective in inhibiting the growth of *Candida* in an environment where Lactobacillus growth is inhibited. This demonstrates that there is utility to such combinations within genital lubricants designed for intra-vaginal use.

With regard to these results, Applicant recognizes that it is possible that the microorganisms which grew on certain media specifically selected for them behaved differently towards the microbicides than they would on neutral media such as TSA because of the delayed material in the media.

However, it should be taken into account that these tests were performed in vitro, under laboratory conditions, using carefully quantified amounts of microorganisms. These ratios are understandably different from those present in natural vaginal flora.

It should be noted that *Candida* in the vagina is commonly associated with vaginal infection, as reported in Danforth's "Obstetrics and Gynecology", sixth edition, published by J. B. Lippincott Company, Philadelphia, 1990, pages 938-9 and 961. Thus on page 938 thereof, it is stated that "*Candida albicans* causes more than 90% of vaginal yeast infections". On page 939 thereof, it is stated that "An overgrowth of these organisms leads to symptomatic vaginitis. Overgrowth is produced by changes in host resistance to local bacterial flora which allows the organism to proliferate". On page 961 thereof, it is further stated that "Candidiasis of the vulva is commonly associated with a vaginal infection".

The above test demonstrates that spermicides destroy the natural flora (Lactobacilli), thus allowing *Candida* in the vagina to proliferate. This can cause ulceration of the vagina, making it more susceptible to HIV penetration into the blood system. It is only the composition in accordance with the invention that inhibits the growth of *Candida* in the absence of natural flora (Lactobacilli).

In vivo tests of a composition containing 0.5% chlorhexidine gluconate and 0.2% methylparaben in accordance with the present invention were also conducted. These tests confirmed that no ulceration or other irregularities occurred in the vaginal tissues of test subjects.

A further test was conducted to determine the sperm motility of the compositions 2, 5, 8 and 9; containing chlorhexidine gluconate, nonoxynol, methylparaben and miconazole nitrate respectively.

Samples comprising 0.2 ml of semen was prepared and placed in a Meckler sperm chamber and covered with a glass slide and observed under a microscope (×100 magnification), such that sperm motion was clearly observable. Subsequently, one or other of the above compositions was added and the specimen was viewed under the microscope to determine the effect of the composition on sperm motility. The test was conducted for all the above compositions, and repeated with semen from three different sources.

For all three semen samples, compositions 2 and 5, containing chlorhexidine gluconate and nonoxynol spermicides respectively, eliminated sperm motility within three minutes. Compositions 8 and 9, containing methylparaben and miconazole nitrate fungicides respectively, did not reduce sperm motility significantly, even after ten minutes.

Considering the results of the two tests discussed above, a skilled person in the art of spermicidal compositions would not have considered adding a fungicide to a antiseptic formulation for use in sexual relations to prevent HIV or other viral infections, since the fungicide would not have any spermicidal or antiviral activity. Nor is there any need for controlling fungi in the vagina, since this is accomplished by the natural flora.

A further experiment was performed to determine the anti-HIV activity of "Gel-X", a genital lubricant in accordance with the present invention.

The reagents and chemicals used were obtained either from Sigma Chemical Company, UK or from BDH Chemicals, UK, with the exception of Natrosol, obtained from Aqualon, care of Honeywill and Stein Ltd.

Gel-X was made up according to the recipe supplied by Pollack International Ltd and contained 0.5% chlorhexidine gluconate, 0.15% methyl paraben, 4.0% propylene glycol, 11.0% glycerin, 1.25% HEC, the remainder being purified water. The cell line C:8166 used, was supplied by MRC Aids Reagent Programme: Experimental *Culture of cell line C8166 and virus HIV-1$_{RF}$*

Cells were cultured in RPMI containing 10% foetal calf serum (FCS). L-Glutamine and penicillin and streptomycin. Cells were passaged every 3-4 days. Prior to use, cells were centrifuged and resuspended in fresh media at $4 \times 10^5$ cells/nd. Virus was grown in the cell line CEM, harvested after 7-10 days, filtered and stored at −70° C. Virus was determined to have a TCID$_{50}$ of $3 \times 10^{10}$/ml on C8166 cells.

Wells of a 96-well tissue culture plate were coated with 100 µl of poly L-lysine (PLL) at 50 µg/ml for 1 hour at room temperature. After 2 washes with phosphate buffered saline (PBS), 50 µl virus (HIV-1$_{RF}$ approx. $1 \times 10^9$ virus particles/ml) was added for a further hour. Wells were washed twice again with PBS followed by the addition of a 10-fold serial dilution of Gel-X. Where indicated, Gel-X was mixed with either 20% seminal plasma or 10% blood. After 1 hour at room temperature, wells were washed 4 times with PBS to ensure removal of all the Gel-X and 200 µl C8166 cells were then added to each well. Plates were cultured for 7 days in a humidified atmosphere at 37° C. with 5% $CO_2$.

Viral infection was determined by measurement of reverse transcriptase activity in the supernatants.

Results

Gel-X was virucidal (i.e. inactivated the virus) when used neat or 1/10. However, the virucidal activity of Gel-X was reduced in the presence of seminal plasma or blood, only providing 100% protection when used neat (i.e. 0.5% chlorhexidine) (Table 1). Despite repeat washing, when used neat, sufficient Gel-X remained bound to the culture plates to be toxic to the indicator cells, demonstrating a lack of selectivity of the agent between viral and cellular membranes. No toxicity was observed when Gel-X was diluted above 1/10

TABLE 1

| Gel-X | Dilution | With 20% SP | | | | With 10% whole blood | |
|---|---|---|---|---|---|---|---|
| | | Mean | SEM | Mean | SEM | Mean | SEM |
| | neat | 34 | 50 | 865 | 702 | 39 | 39 |
| | 1:10 | 46 | 43 | 5260 | 1872 | 14436 | 43 |
| | 1:100 | 26379 | 2746 | 7326 | 1966 | 13397 | 23 |
| | 1:1000 | 23972 | 2285 | 11371 | 2727 | 15156 | 1057 |
| | 1:10000 | 25425 | 2794 | 27254 | 5414 | 25049 | 1125 |
| | 1:100000 | 12855 | 2293 | 34285 | 7484 | 20038 | 1255 |
| Virus control | 0 | 21138 | 2885 | 16859 | 4513 | 18541 | 2649 |

CONCLUSION

These results demonstrate that Gel-X is active against HIV when used neat of 1/10. These findings are in agreement with previous studies demonstrating that chlorhexidine has an $IC_{50}$ value (50% inhibitory dose) of 0.25 μM, a $CC_{50}$ value (50% toxic dose) of 1.3 μM and a selectivity value of 5.2 (Int J STD & AIDS). The effects of semen and blood on the anti-HIV activity of Gel-X are similar to those reported for the anti-bacterial effects of chlorhexidine (Sex Trans diseases 2000, 27:74-78). In summary, Gel-X is likely to inactivate cell free and cell associated HIV in vivo.

For maximum safety, it is suggested that the lubricant composition of the present invention be used together with other prophylactic means, such as condoms or diaphragms, to provide an additional safety margin, in case the conventional devices are defective. Furthermore, the increased lubrication provided by the composition of this invention is an additional benefit from its use. The antiseptic lubricant can also be used by doctors and in hospitals to lubricate gloves or instruments before examining the vagina, rectum or mouth.

What is claimed is:

1. A method for providing for safe sexual relations and reducing HIV transmission facilitated by spermicide-induced vaginal ulcers, comprising applying to sexual organs prior to sexual relations a lubricant composition consisting essentially of:
   a) lubricant effective to reduce friction, thereby reducing the rupture of blood vessels during sexual relations,
   b) an effective amount of spermicide active against HIV and other viruses, said spermicide destroying the human immunodeficiency virus and other viruses, said spermicide immobilizing the sperm and reacting with vaginal mucosa to form a barrier to the penetration of sperm cells into the uterus, said spermicide also destroying natural flora in the vagina and permitting thereby growth of fungi causing ulceration of the vagina;
   c) an effective amount of a fungicide to prevent the growth of the fungi in the vagina which grow in the absence of natural bacterial flora destroyed by the spermicide; and optionally, water, alcohol and flavors;
   said composition having no substantial detrimental effect.

2. A method according to claim 1, wherein the spermicide is chlorhexidine or a salt thereof.

3. A method according to claim 2, wherein the spermicide is chlorhexidine or a salt thereof in a concentration of between 0.1% and 5.0% of the lubricant.

4. A method according to claim 2, wherein the spermicide is chlorhexidine or a salt thereof in a concentration of between 0.2% and 0.6% of the lubricant.

5. A method according to claim 1, wherein the chlorhexidine salt is the gluconate or digluconate salt.

6. A method according to claim 1, wherein the lubricant is propylene glycol, glycerin or a mixture thereof.

7. A method according to claim 1, wherein the lubricant comprises between 7% and 21% of the lubricant composition.

8. A method according to claim 1, wherein the fungicide is methyl paraben.

9. A method according to claim 1, wherein the fungicide is present in an amount of between 0.25% and 1.0% of the lubricant composition.

10. A method according to claim 1, wherein the lubricant composition has a pH corresponding to that of the vagina.

11. A method according to claim 1, wherein the lubricant composition further comprises alcohol.

12. A method according to claim 1, wherein the lubricant composition is water soluble.

13. A method according to claim 1, wherein the lubricant consists essentially of:

| | |
|---|---|
| Chlorhexidine salt | 0.1% to 5% |
| Methylparaben | 0.25% to 1.0% |
| Propylene glycol | 2.0% to 6% |
| Glycerine | 5.0% to 15% |
| CMC or HEC | 0.5% to 2.0% |
| Purified water | to 100%. |

14. A method according to claim 1, wherein the lubricant composition consists essentially of:

| | |
|---|---|
| Chlorhexidine digluconate | 0.2% to 0.6% |
| Methylparaben | 0.25% |
| Propylene glycol | 4.0% |
| Glycerin | 11.0% |
| HEC | 1.25% |
| Purified water | to 100%. |

15. A method according to claim 1, wherein the lubricant composition consists essentially of:

| | |
|---|---|
| Chlorhexidine Gluconate | 0.50% |
| Methyl Paraben | 0.25% |
| Glycerine | 11.00% |
| Propylene Glycol | 4.00% |
| Natrosol HHRB | 1.25% |
| Deionized Water | 83.00%. |

* * * * *